United States Patent [19]
Masaki et al.

[11] Patent Number: 5,965,753
[45] Date of Patent: Oct. 12, 1999

[54] PROCESS FOR PREPARATION OF GLYCIDYL SULFONATE DERIVATIVE

[75] Inventors: Midori Masaki, Amagasaki; Yoshiro Furukawa, Osaka; Keishi Takenaka, Amagasaki, all of Japan

[73] Assignee: Daiso Co., LTd., Tokyo, Japan

[21] Appl. No.: 09/101,878

[22] PCT Filed: Jan. 17, 1997

[86] PCT No.: PCT/JP97/00075

§ 371 Date: Jul. 20, 1998

§ 102(e) Date: Jul. 20, 1998

[87] PCT Pub. No.: WO97/26254

PCT Pub. Date: Jul. 24, 1997

[30] Foreign Application Priority Data

Jan. 19, 1996 [JP] Japan ................... 8-007356

[51] Int. Cl.$^6$ ................... C07D 303/34
[52] U.S. Cl. ........... 549/513; 549/520; 549/521; 549/554; 549/555; 549/556; 549/560
[58] Field of Search ................ 549/513, 520, 549/521, 554, 555, 556, 560

[56] References Cited

U.S. PATENT DOCUMENTS 4,946,974  8/1990  Sharpless et al. ............... 549/551
5,252,759  10/1993  Shum .......................... 549/541

FOREIGN PATENT DOCUMENTS

A-6-179663  1/1993  Japan .
A-6-306067  1/1993  Japan .
A-7-165743  9/1993  Japan .

OTHER PUBLICATIONS

Klunder et al., *J. Org. Chem*, 1989, 54, 1295–1304, "Arenesulfonate Derivatives of Homochiral glycidol Versatile Chiral Building Blocks for Organic Synthesis."

Klunder et al., *J. Org. Chem.*, 1986, 51, 3710–3712, "Asymmetric Epoxidation of Allyl Alcohol: Efficient Routes to Homochiral β–Adrenergic Blocking Agents."

*Primary Examiner*—Johann Richter
*Assistant Examiner*—John F. Dolan
*Attorney, Agent, or Firm*—Jacobson, Price, Holman & Stern, PLLC

[57] ABSTRACT

A process for preparation of a glycidyl sulfonate derivative with high purity and in high yield, which is characterized in reacting glycidol which is prepared from treating 3-chloro-1,2-propanediol in an aqueous solvent in the basic condition, without isolating the resulting glycidol with a sulfonyl halide in a two phase solvent consisting of an organic solvent and water in the presence of an inorganic base and a tertiary amine or a pyridine derivative.

10 Claims, No Drawings

PROCESS FOR PREPARATION OF GLYCIDYL SULFONATE DERIVATIVE

This application is a 371 of PCT/JP97/00075, dated Jan. 17, 1987.

FIELD OF ART

The present invention relates to an improved process for preparation of a glycidyl sulfonate derivative. The glycidyl sulfonate derivative is useful as an intermediate for medicines, agricultural chemicals and biologically active substances.

BACKGROUND OF ART

A glycidyl sulfonate derivative is generally prepared by reacting glycidol with a sulfonyl chloride in the presence of a tertiary amine in a solvent selected from an aromatic hydrocarbon and a halogenated hydrocarbon. For example, methods of the reaction in dichloromethane or toluene are known (J. Org. Chem., 51, 3710 (1986), J. Org. Chem., 54, 1295 (1989) and U.S. Pat. No. 4,946,974). However, according to these methods, glycidol as a starting material is unstable and the side-reaction such as dimerization occurs. The product, therefore is produced with many impurities. To obtain the product with high purity, rectification or repeated recrystallization is required and eventually decrease of the yield occurs. As these methods have many demerits in the industrial scale as mentioned above, an effective method has been desired. Recently a method for preparing the product by reacting glycidol with an organic sulfonyl halide in the presence of a tertiary amine in a two phase solution consisting of water and toluene has been proposed (Japanese Patent Publication A No. 306067/1994). But the reaction rate is low and purity of the product is not satisfied. And after preparing glycidol, an intermediate, further to extract it with water is necessary and the procedure is inconvenient. To solve these inconveniences the present inventors have proposed a method for preparing glycidyl tosylate by treating 3-chloro-1,2-propanediol with an alkali metal carbonate in an organic solvent and without isolation of the resulting glycidol, subjecting it to reaction with p-toluenesulfonyl chloride, a tertiary amine and 4-dimethylaminopyridine to produce glycidyl tosylate (Japanese Patent Publication A No. 165743/1995). However, the method has following practical disadvantages: The reaction rate is low in case of treating with an alkali metal carbonate, side-reaction occurs to give the compound with many impurities and further the viscosity of the reaction mixture is too increased in case of using a solvent except for a halogenated solvent.

The present inventors, further extensively engaged in study for solving the above problems to find that an objective glycidylsulfonate with high purity and in good yield was obtained by using a two phase solvent consisting of an organic solvent and water and in the presence of a specific inorganic base and a tertiary amine or a pyridine derivative in case of reacting glycidol with a sulfonyl halide and thus this invention was completed. The present inventors, further found the method for preparing an objective glycidyl sulfonate derivative more conveniently and efficiently by reacting glycidol, an intermediate, with 3-chloro-1,2-propanediol under the specific basic condition in an aqueous solvent and without separating the resulting glycidol, subjecting it to reaction with the above sulfonyl halide.

DISCLOSURE OF INVENTION

The present invention provides to an improved process for preparation of a glycidylsulfonate derivative which is characterized in reacting glycidol with a sulfonyl halide in a two phase solvent consisting of an organic solvent and water in the presence of at least one in organic base selecting from of an alkali metal or alkaline earth metal hydroxide, an alkali metal or alkaline earth metal carbonate and an alkali metal or alkaline earth metal hydrogen carbonate, and a tertiary amine or a pyridine derivative.

The preferable mode of this invention relates to a process for preparation of a glycidyl sulfonate derivative in one reaction vessel which is characterized in reacting with 3-chloro-1,2-propanediol in an aqueous solvent in the presence of at least an inorganic base selecting from an alkali metal or alkaline earth metal hydroxide, an alkali metal or alkaline earth metal carbonate and an alkali metal or alkaline earth metal hydrogen carbonate, and without isolating the resulting glycidol, subjecting it to reaction with the above sulfonyl halide to obtain directly an objective compound.

According to this invention, glycidol, an intermediate, is used in an optically active form or a racemate. In case of using an optically active glycidol, an objective glycidyl sulfonate is directly obtainable in the optically active form. Therefore, this method is preferable. Furthermore, in case of using optically active 3-chloro-1,2-propanediol as a starting material, an optically active glycidyl sulfonate is more conveniently obtainable.

The process of this invention by using 3-chloro-1,2-propanediol as a starting material is shown by the following scheme.

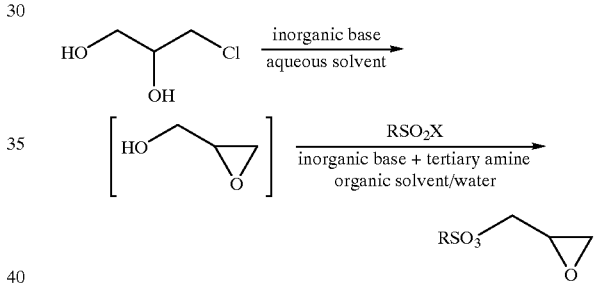

In the above formula, R is an aliphatic hydrocarbon or an aromatic hydrocarbon, and X is a halogen atom.

According to the process of this invention, as shown by the above reaction scheme, first the cyclization occurs by treating 3-chloro-1,2-propanediol with an inorganic base in an aqueous solvent to produce glycidol, an intermediate. And then by reacting glycidol with a sulfonyl halide, that is, sulfonating a hydroxy group of glycidol in the presence of a combination of an inorganic base and a tertiary amine in a two phase solvent consisting of an organic solvent and water, there is obtained a glycidyl sulfonate.

The cyclization of 3-chloro-1,2-propanediol is carried out in the basic condition in an aqueous solvent (usually in water). In this reaction, as a base there is used an alkali metal hydroxide, an alkaline earth metal hydroxide, an alkali metal carbonate, an alkaline earth metal carbonate, an alkali metal hydrogen carbonate or an alkaline earth metal hydrogen carbonate, or a mixture thereof, e.g. lithium hydride, sodium hydroxide, potassium hydroxide, calcium hydroxide, lithium carbonate, sodium carbonate, potassium carbonate, calcium carbonate, lithium hydrogen carbonate, sodium hydrogen carbonate, potassium hydrogen carbonate, preferably an alkali metal hydroxide, especially preferably sodium hydroxide or potassium hydroxide. The amount of a base used in this reaction is 1 mol or more than 1 mol equivalent, usually 1.0–10.0 mol equivalents, preferably 1.0–4.0 mol equivalents to 3-chloro-1,2-propanediol. In case of using the base less than 1 mol equivalent, the reaction is not completed and in case of using the base more than 10 mol equivalents, side-reaction occurs much. The temperature at the cyclization is 0–40° C., preferably 15–30° C. In case of reacting at lower temperature than at a range of the above temperatures, the reaction rate is low and in case of reacting at higher temperature than at a range of the above temperatures, a dimer of a starting material or glycerine forms as a by-product and the yield decreases.

This reaction is carried out by dropping 3-chloro-1,2-propanediol diluted with water or without dilution, to an aqueous solution of the above base and by stirring the mixture. On the other hand this reaction may be carried out by dropping an aqueous solution of the above base to 3-chloro-1,2-propanediol diluted with water and by stirring the mixture. The concentration of an aqueous solution of 3-chloro-1,2-propanediol is preferably 5–90% by weight. In less than the concentration of the above range, the reaction is not efficiently and not practical due to a poor volume efficiency. In more than the concentration of the above range, by-products increase. The reaction is usually completed in 1–24 hours to give glycidol, an intermediate, and then following substitution reaction is carried out.

The reaction for preparing a glycidyl sulfonate from glycidol is completed as follows. To an aqueous reaction mixture containing glycidol prepared by the above method, a tertiary amine or a pyridine derivative is added, and if necessary, an inorganic base is added, and a sulfonyl halide which is dissolved in an organic solvent is added dropwise to the mixture in the presence of a combination of an inorganic base and a tertiary amine or a pyridine derivative to give a glycidyl sulfonate. The above addition of an inorganic base may be carried out, after a tertiary amine or a pyridine derivative is added to the reaction mixture containing glycidol and thereto a sulfonyl halide dissolved in an organic solvent is dropped. Even other method is included in this process, as long as the reaction with a sulfonyl halide is carried out essentially in the presence of a combination of an inorganic base and a tertiary amine or a pyridine derivative in a two phase solvent consisting of an organic solvent and water.

Instead of starting from pre-reaction of the above reaction and carrying a sequence of reactions in the conversion from glycidol to a glycidyl sulfonate, in case of sulfonating commercially available glycidol, a glycidyl sulfonate is obtainable by dropping a solution of a sulfonyl halide in an organic solvent to an aqueous glycidol solution in the presence of the combination of an inorganic base and a tertiary amine or a pyridine derivative to carry out reaction. In this procedure, an inorganic base and a tertiary amine or a pyridine derivative may be added simultaneously or separately to the reaction system. For example, a tertiary amine or a pyridine derivative is dissolved in an organic solvent together with a sulfonyl halide and the obtained solution is added to an aqueous glycidol solution to which an inorganic base is previously added, or an inorganic base may be added to the reaction system after the solution containing a sulfonyl halide is dropped.

Examples of a sulfonyl halide used in this reaction, are an aliphatic hydrocarbon (having 1–6 carbon atoms) sulfonyl halide, such as methanesulfonyl chloride, ethanesulfonyl chloride, etc., a substituted or unsubstituted phenyl or naphthyl sulfonyl halide, such as benzenesulfonyl chloride, p-toluenesulfonyl chloride, 3-nitrobenzenesulfonyl chloride, 4-chlorobenzenesulfonyl chloride, etc., and said substituents are an alkyl having 1–4 carbon atoms, an alkoxy having 1–4 carbon atoms, a halogen atom, nitro, cyano and so on.

The amount of a sulfonyl halide used in this reaction, is 0.6–1.5 mol equivalents, preferably 0.8–1.2 mol equivalents to glycidol. When glycidol is prepared from 3-chloro-1,2-propanediol and without isolation of the resulting glycidol it is reacted with a sulfonyl halide, the amount of a sulfonyl halide is 0.6–1.5 mol equivalents, preferably 0.8–1.2 mol equivalents to 3-chloro-1,2-propanediol, a starting material. The yield decreases in case of shortage of the lower limit of the amount and the excess of the sulfonyl halide remains in the reaction system of the reaction and purity of an objective compound is down in case of excess of the upper limit of the amount.

An inorganic base used in this reaction is illustrated the same inorganic base as one is used in the above reaction for preparing glycidol, for example an alkali metal hydroxide, an alkaline earth metal hydroxide, an alkali metal carbonate, an alkaline earth metal carbonate, an alkali metal hydrogen carbonate or an alkaline earth metal hydrogen carbonate, or a mixture thereof, e.g. lithium hydride, sodium hydroxide, potassium hydroxide, calcium hydroxide, lithium carbonate, sodium carbonate, potassium carbonate, calcium carbonate, lithium hydrogen carbonate, sodium hydrogen carbonate, potassium hydrogen carbonate, preferably an alkali metal hydroxide, especially preferably sodium hydroxide or potassium hydroxide. The amount of a base used in this reaction is 0.6 mol or more than 0.6 mol equivalent, usually 0.8–6.0 mol equivalents, preferably 1.0–4.0 mol equivalents to glycidol. In case of using the base less than 0.6 mol equivalent, the reaction is not completed and in case of using the base more than 6.0 mol equivalents, side-reaction occurs much. An inorganic base used in this reaction may be the same one or different one as one is used in the above cyclization. The whole amount or the amount in part used in sulfanation of glycidol may be added together with the amount of the base necessary for the cyclization. However, even in this case the amount of the base is preferably 1.0–10.0 mol equivalents to 3-chloro-1,2-propanediol.

Examples of tertiary amines used together with the above inorganic base are a trialkylamine in which each alkyl portion has 1–6 carbon atoms, such as trimethylamine, N,N-dimethylethylamine, N,N-diethylmethylamine, triethylamine, tripropylamine, N,N-dimethylisopropylamine, ethyldiisopropylamine, N,N-dimethylcyclohexylamine, N,N-diethylcyclohexylamine, N-methyldicyclohexylamine, N,N-dimethylhexylamine, N,N-diethylhexylamine, dialkylphenylamine or monoalkyldiphenylamine in which each alkyl portion has 1–4 carbon atoms, such as N,N-dimethylaniline, N,N-diethylaniline, N-methyl-N-ethylaniline, N-methyldiphenylamine, and a saturated heterocycle which contains a nitrogen atom substituted by an alkyl having 1–4 carbon atoms, such as 1-methylpyrrolidine, 1-butylpyrrolidine, 1-methylpiperidine, 1-ethylpiperidine, 4-methylmorpholine, 4-ethylmorpholine, etc.

Examples of pyridine derivatives are pyridine, a pyridine substituted by 1–3 alkyl groups in which each the group having 1–4 carbon atoms, such as 2-picoline, 2-t-butylpyridine, 4-ethylpyridine, 4-t-butylpyridine, 2,6-lutidine, 2,4,6-collidine, a pyridine substituted by 1–3 alkoxy groups in which each the group having 1–4 carbon atoms, such as 2-methoxypyridine, 2-butoxypyridine, 4-methoxypyridine, 2,6-dimethoxypyridine, and a pyridine substituted by a dialkylamino group in which each alkyl has 1–4 carbon atoms, such as 2-N,N-dimethylaminopyridine, 3-N,N-dimethylaminopyridine, 4-N,N- dimethylaminopyridine, 4-N,N-diethylaminopyridine, 4-N-methyl-N-ethylaminopyridine.

The amount thereof is 0.5–30 mol %, preferably 1.0–20 mol % toglycidol. When glycidol is prepared from 3-chloro-1,2-propanediol and without isolation of the resulting glycidol it is reacted with a sulfonyl halide, the amount of a sulfonyl halide is 0.5–30 mol %, preferably 1–20 mol % to 3-chloro-1,2-propanediol. The reaction period becomes extremely long and the yield decreases in case of shortage of the lower limit of the amount of the tertiary amine or the pyridine derivative, and side-reaction occurs in the reaction system and purity of an objective compound is down in case of excess of the upper limit of the amount. When the reaction is carried out with a tertiary amine without any inorganic base, like a method carried out in the two phase (water/toluene) shown in the above mentioned Japanese Patent Publication A No. 306067, the reaction rate is low and many impurities form.

As organic solvents used in sulfonation of glycidol are illustrated solvents which dissolve a sulfonyl halide, do not react with it and do not dissolve in water, such as a halogenated hydrocarbon, e.g. dichloromethane, 1,2-dichloroethane, 1,1-dichloroethane, chloroform etc., an ether, e.g. diethyl ether, t-butylmethyl ether, diisopropyl ether, a ketone, e.g. methyl ethyl ketone, methyl isobutyl ketone, an ester, e.g. ethyl acetate, butyl acetate, and an aromatic hydrocarbon, e.g. benzene, toluene, xylene, a mixture thereof.

The sulfonation of the above glycidol is carried out usually at –10–40° C., preferably 0–10° C. The progress of the reaction is slow at the temperature lower than the above lower limited temperature. At the higher temperature than the above upper limited temperature, side-reaction, such as hydrolysis of the resulting glycidyl sulfonate occurs and the yield decreases significantly.

After completion of the reaction, the reaction mixture is poured into a separating funnel, followed by treatment with an inorganic acid, e. g. hydrochloric acid, sulfuric acid to give a glycidyl sulfonate in an organic layer.

The organic solvent is evaporated, the residue is subjected to the conventional purification, such as distillation and recrystallization to give a glycidyl sulfonate with high purity.

When an optically active 3-chloro-1,2-propanediol or glycidol is used, there is obtained an optically active glycidyl sulfonate. When 3-chloro-1,2-propanediol or glycidol with highly optical purity is used as a starting material, in the course of the reaction racemization does not almost occur and glycidyl sulfonate with very highly optical purity is obtained. 3-Chloro-1,2-propanediol with very highly optical purity (more than 98% ee) is prepared in the manner described in Japanese Patent Publication B No. 73998/1992 and No. 73999/1992.

That is, the genus Pseudomonas or Alcaligenes which can grow as a carbon source of (S) or (R) 3-halogeno-1,2-propanediol is cultured in a medium containing racemic 3-halogeno-1,2-propanediol as only a carbon source and remaining (R) or (S)-3-halogeno-1,2-propanediol is separately obtained.

According to the process of this invention, (S)-glycidyl sulfonate is obtained via (R)-glycidol from (R)-3-chloro-1, 2-propanediol, and (R)-glycidyl sulfonate is obtained via (S)-glycidol from (S)-3-chloro-1,2-propanediol.

EXAMPLE

This invention is in detail explained in the following examples, but the invention is not limited to the examples.

Example 1
Preparation of Glycidyl Tosylate

To a solution of 10 g of 3-chloro-1,2-propanediol (0.09 mol) and 40 ml of water, was added dropwise at 24–26° C. 16.6 g of 24% sodium hydroxide (0.1 mol). The solution was stirred for one hour. The solution was cooled and thereto 0.17 g of N,N-dimethylaminopyridine (0.0014 mol) and 17.2 g of p-toluenesulfonyl chloride (0.09 mol) in 50 ml of toluene, and then 16.6 g of 24% sodium hydroxide (0.1 mol) were added under stirring at 0–5° C. And the solution was stirred for one hour. After separation with a separating funnel, the organic layer was washed with 50 ml of 1% hydrochloric acid and 50 ml of water. The excess solvent was removed under vacuo. The chemical purity by HPLC at that time was 98.3%. The residue was recrystallized from isopropyl alcohol/hexane=1/1 (V/V) to give 14.0 g of glycidyl tosylate. Chemical purity: 99.6% (yield: 68%)

Example 2
Preparation of Optically Active Glycidol

The reaction was carried out as the same as in the Example 1, except for using optically active (R)-3-chloro-1,2-propanediol (optical purity: 98.6% ee) instead of 3-chloro-1,2-propanediol. Chemical purity and optical purity of the product by HPLC before recrystallization were 98.5%, 97.3% ee respectively. By recrystallization there were obtained 15.5 g of (S)-glycidyl tosylate (chemical purity: 99.8%, optical purity: 98.3% ee, yield. 75%)

Example 3
Preparation of Optically Active Glycidyl Nosylate

To a solution of 10 g of (R)-3-chloro-1,2-propanediol (0.09 mol) (optical purity: 98.7% ee) and 40 ml of water were added dropwise at 26° C. 15.1 g of 24% sodium hyroxide (0.09 mol) and the solution was stirred for one hour. The reaction solution was cooled and thereto 0.17 g of N,N-dimethylaminopyridine (0.0014 mol) and 20 g of m-nitrobenzenesulfonyl chloride (0.09 mol) in 90 ml of toluene, and then 16.6 g of 24% sodium hydroxide (0.1 mol) were added under stirring at 0–5° C. And the solution was stirred for one hour. After separation with a separating funnel, the organic layer was washed with 50 ml of 1% hydrochloric acid and 50 ml of water. The excess solvent was removed under vacuo. The chemical purity and optical purity at that time were 97.2%, 97.5% ee respectively. The residue was recrystallized from ethyl acetate/lexane=1/1 (V/V) to give 16.4 g of (S)-glycidyl nosylate (yield 70%). Chemical purity: 98.4%, Optical purity: 98.9% ee

Example 4
Peparation of Optically Active Glycidyl Tosylate

To a solution of 6.7 g of (R)-glycidol (0.09 mol)(optical purity: 99.4% ee) and 50 ml of water, 0.17 g of N,N-dimethylaminopyridine (0.0014 mol) and 17.2 g of p-toluenesulfonyl chloride (0.09 mol) in 50 ml of toluene, and then 18.1 g of 24% sodium hydroxide (0.11 mol) were added under stirring at 0–5° C. And the solution was stirred for one hour. After separation with a separating funnel, the organic layer was washed with 50 ml of 1% hydrochloric acid and 50 ml of water. The excess solvent was removed under vacuo. The chemical purity by HPLC and optical purity at that time were 99.5%, 99.5% ee respectively. The residue was recrystallized from isopropyl alcohol/hexane= 1/1 (V/V) to give 16.1 g of (S)-glycidyl tosylate (yield 78%). Chemical purity: 99.9%, Optical purity: 99.6% ee

Comparative Example 1

The reaction was carried out as the same as in Example 1 except for reacting without N,N-dimethylaminopyridine and stirring for 70 hours after completion of addition of sodium hydroxide. As a result much of p-toluenesulfonyl chloride remained without reaction and the chemical purity of glycidyl tosylate before recrystallization was very low, 46.8%.

Comparative Example 2

To a solution of 10 g of 3-chloro-1,2-propanediol (0.09 mol) and 40 ml of water, was added dropwise at 24–25° C. 16.6 g of 24% sodium hydroxide (0.1 mol). The solution was stirred for one hour. The reaction solution was cooled and thereto 0.17 g of N,N-dimethylaminopyridine (0.0014 mol), 17.2 g of p-toluenesulfonyl chloride (0.09 mol) in 50 ml of toluene, and then 10.1 g of triethylamie (0.1 mol) without using sodium hydroxide were added in order under stirring at 0–5° C. The reaction was kept for 20 hours, but the reaction was not completed and unreacted p-toluenesulfonyl chloride remained. In addition to that, the chemical purity of obtained glycidyl tosylate before recrystallization was low, 59.3%.

Comparative Example 3

To a suspension of 37.5 g of potassium carbonate (0.27 mol) and 250 ml of 1,2-dichloroethane, was added dropwise at 24–28° C. 20 g of (S)-3-chloro-1,2-propanediol (0.18 mol) (optical purity: 98.9% ee). After finishing the addition, the solution was stirred for 26 hours and cooled. To the reaction solution were added dropwise under stirring at 5–10° C. 20.1 g of triethylamine (0.2 mol) and 0.4 g of N,N-dimethylaminopyridine (0.0033 mol) and 34.5 g of p-toluenesulfonyl chloride (0.18 ml) in order. After finishing the addition the mixture was stirred for 3 hours and the resulting salt was dissolved by adding 150 ml of 3% hydrochloric acid. The organic layer was washed with 150 ml of 1% hydrochloric acid and 150 ml of water. The excess solvent was removed under vacuo. The chemical purity and optical purity at that time were 93.7%, 96.6% ee respectively. The residue was recrystallized from isopropyl alcohol/hexane=1/1 (V/V) to give 28.9 g of (S)-glycidyl tosylate (yield 70%). Chemical purity: 98.3%, optical purity: 97.5% ee

We claim:
1. A process for preparation of a glycidyl sulfonate derivative of the formula

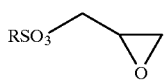

wherein R is an aliphatic hydrocarbon or an aromatic hydrocarbon,
comprising reacting glycidol with a sulfonyl halide in a two phase solvent comprising of an organic solvent and water in the presence of at least one inorganic base selecting from an alkali metal hydroxide, an alkaline earth metal hydroxide, an alkali metal carbonate, an alkaline earth metal carbonate, an alkali metal hydrogen carbonate and an alkaline earth metal hydrogen carbonate, and a tertiary amine or a pyridine derivative.

2. The process for preparing a glycidyl sulfonate derivative of the formula

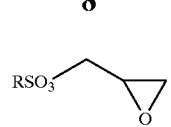

in which R is as defined above,
according to claim 1 wherein the sulfonyl halide is p-toluenesulfonyl chloride or m-nitrobenzenesulfonyl chloride.

3. The process for preparing a glycidyl sulfonate derivative of the formula

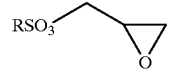

in which R is as defined above,
according to claim 1 wherein the pyridine derivative is N,N-dimethylaminopyridine.

4. The process for preparing a glycidyl sulfonate derivative of the formula

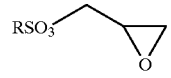

in which R is as defined above,
according to claim 1 wherein the inorganic base is sodium hydroxide and/or potassium hydroxide.

5. The process for preparing a glycidyl sulfonate derivative of the formula

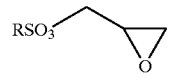

in which R is as defined above,
according to claim 1 wherein the gylcidol is an optically active form.

6. A process for preparation of a glycidyl sulfonate derivative of the formula

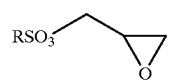

wherein R is an aliphatic hydrocarbon or an aromatic hydrocarbon,
comprising reacting 3-halogeno-1,2-propanediol in an aqueous solvent in the presence of at least one inorganic base selected from an alkali metal hydroxide, an alkaline earth metal hydroxide, an alkali metal carbonate, an alkaline earth metal carbonate, an alkali metal hydrogen carbonate and an alkaline earth metal hydrogen carbonate, and without isolating the resulting glycidol, subjecting it to reaction with a sulfonyl halide in a two phase solvent consisting of an organic solvent and water in the presence of the above inorganic base and a tertiary amine or a pyridine derivative.

7. The process for preparing a glycidyl sulfonate derivative of the formula

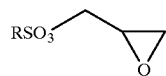

in which R is as defined above, according to claim 6 wherein the sulfonyl halide is p-toluenesulfonyl chloride or m-nitrobenzenesulfonyl chloride.

8. The process for preparing a glycidyl sulfonate derivative of the formula

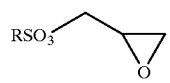

in which R is as defined above, according to claim 6 wherein the pyridine derivative is N,N-dimethylaminopyridine.

9. The process for preparing a glycidyl sulfonate derivative of the formula

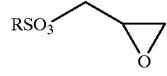

in which R is as defined above, according to claim 6 wherein, the inorganic base is sodium hydroxide and/or potassium hydroxide.

10. The process for preparing a glycidyl sulfonate derivative of the formula

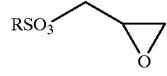

in which R is as defined above, according to claim 6 wherein the glycidol is an optically active form.

* * * * *